United States Patent [19]

Kogure et al.

[11] 4,096,338
[45] Jun. 20, 1978

[54] BUTENOIC AND PYRUVIC ACID DERIVATIVES

[75] Inventors: Katsura Kogure, Kawagoe; Noriyoshi Sueda, Tokyo; Sizuo Himoto, Kawagoe; Youziro Yoshino, Tokyo; Kunio Nakagawa, Kawagoe, all of Japan

[73] Assignee: Nisshin Flour Milling Co., Ltd., Tokyo, Japan

[21] Appl. No.: 743,062

[22] Filed: Nov. 18, 1976

Related U.S. Application Data

[62] Division of Ser. No. 599,775, Jul. 28, 1975, Pat. No. 4,016,196.

[30] Foreign Application Priority Data

Jul. 27, 1974 Japan .................................. 49-85622
Jul. 29, 1974 Japan .................................. 49-86001

[51] Int. Cl.² ............................................. C07C 69/76
[52] U.S. Cl. .................................................... 560/59

[58] Field of Search ..................................... 260/473 A

[56] References Cited

U.S. PATENT DOCUMENTS

3,655,743  4/1972  Nickl et al. ...................... 260/473 A
3,754,021  4/1973  Shen et al. ....................... 260/473 A

*Primary Examiner*—Paul J. Killos
*Attorney, Agent, or Firm*—Haseltine, Lake & Waters

[57] ABSTRACT

2-Hydroxy-butenoic acid derivatives of the general formula:

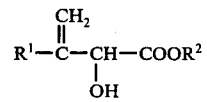

are described. These compounds have antiphlogistic activity.

1 Claim, No Drawings

BUTENOIC AND PYRUVIC ACID DERIVATIVES

This is a division of U.S. Ser. No. 599,775, filed July 28, 1975 now U.S. Pat. No. 4,016,196.

This invention relates to the treatment of a certain glycidic acid derivative by heating thereby to produce a new 2-hydroxy butenoic acid derivative or optionally a new peruvic acid derivative.

In accordance with one embodiment of the invention, a glycidic acid derivative having the general formula (I)

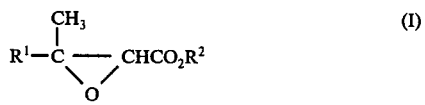

wherein $R^1$ is a group selected from aliphatic, alicyclic and aromatic groups, and $R^2$ is a lower alkyl group, is subjected to heating at a temperature of at least 140° C., thereby to form a 2-hydroxy butenoic acid derivative of the general formula (II)

wherein $R^1$ and $R^2$ are defined as above.

In another embodiment of the invention, a glycidic acid ester of the general formula (I) as above is heated in the presence of an electrophilic reagent thereby to form a pyruvic acid derivative of the general formula (III)

wherein $R^1$ and $R^2$ are same as defined before.

In one specific embodiment of the present invention, a butenoic acid ester of the general formula (II) which may have been produced according to the first embodiment is heated in the presence of an electrophilic reagent thereby to form a pyruvic acid derivative of the general formula (III) as above.

Heretofore, we made studies on the reactions of compounds of the aforesaid formula (I) to find that when the compound of the formula (I) is heated to at least 140° C., the conversion of said compound to the compound of the formula (II) takes place substantially quantitatively. If, in this case, the temperature is below 140° C., such conversion reaction as mentioned above does not occur at all. On the other hand, when the compound of the formula (I) is treated at normal or elevated temperature in the presence of such substance as Lewis acid or sulfuric acid, the conversion of said compound to the compound of the formula (II) takes place as well. We further conducted systematic studies to confirm that when the compound of the formula (I) is heated in the presence of an electrophilic reagent, not the compound of the formula (II) but the keto-acid structure compound of the formula (III) is obtained, and that the same result is obtained even when the compound of the formula (I) is replaced by the compound of the formula (II). Accordingly, all the reactions which take place in the present invention are considered to belong to novel electron-withdrawing reactions, though the reaction mechanism thereof has not been elucidated in detail yet.

The present invention is not restricted in reaction mechanism so far as the construction thereof is as set forth in the claim. According to our investigation, however, the conversion of the compound of the formula (I) to the compound of the formula (III) in the presence of an electrophilic reagent is not always accomplished through the compound of the formula (II), and it is imagined that specific reactions exist competitively at least in part.

The compound that is used as the starting material in the present invention is a compound of the aforesaid formula (I), wherein $R^2$ is a lower alkyl group, e.g. methyl, ethyl, n-propyl, isopropyl, n-butyl, tert-butyl, isobutyl or the like alkyl group having up to 4 carbon atoms, and $R^1$ is an alkyl (saturated or unsaturated, straight chain or branched-chain alkyl), cycloalkyl or aryl (including alkaryl and aralkyl) group. Concrete examples of the group represented by $R^1$ are methyl, ethyl, propyl, isopropyl, n-butyl, sec-butyl, tert-butyl, amyl, hexyl, heptyl, octyl, decyl, dodecyl, octadecyl, vinyl, allyl, methallyl, butenyl, pentenyl, hexenyl, heptenyl, octenyl, ethynyl, propinyl, cyclobutyl, cyclopentyl, cyclohexyl, methylcyclohexyl, cycloheptyl, cyclooctyl, cyclodecyl, cycloundecyl, cyclododecyl, cyclopentadecyl, phenyl, tolyl, xylyl, benzyl, phenetyl, phenylpropyl, naphthylmethyl, o-carboxybenzyl, and condensed and crosslinked ring structure groups such as indanyl, indenyl, naphthyl, phenanthryl, cyclopentanopolyhydrophenanthryl, adamantanyl, bicyclo(3:1:1-)heptyl and bicyclo(2:2:2)octyl. All these groups may be unsubstituted or may be substituted by one or more substituents which do not interfere with the intended reactions. Examples of such substituents are alkoxy groups such as methoxy, ethoxy, propoxy and butoxy; acyloxy groups such as acetoxy, propionoxy and butyroxy; nitro groups; alkylamino groups such as dimethylamino; and halogens such as fluorine, chlorine and bromine. Particularly important as the groups represented by $R^1$ are p-alkylphenyls including p-methylphenyl; 4-biphenylyl; 4-cyclohexylphenyl; 3-phenoxyphenyl; 4′-fluoro-4-biphenylyl; 2-fluoro-4-biphenylyl; 3-benzoylphenyl; and 6-methoxy-2-naphthyl.

The compound of the general formula (I), which is one starting material used in the present invention is prepared by, for example, reacting an acetophenone derivative of the general formula $R^1$—$COCH_3$ (wherein $R^1$ is as defined previously) with a 2-halogenated acetic acid ester of the general formula $XCH_2CO_2R^2$ (wherein $R^2$ is as defined previously). The above-mentioned reaction is carried out under the conditions of Darzens' reaction, and is preferably effected under anhydrous conditions in an inert gas atmosphere in the presence of an alkali condensing agent. As the condensing agent, there may be used sodium methoxide, sodium ethoxide, sodium isopropoxide or sodium amide.

When treated with, for example, sulfuric acid at normal temperature, the thus obtained compound of the formula (I) can easily give the compound of the formula (II), which is another starting compound used in the present invention.

All such starting compounds (I) as mentioned previously can be subjected to the novel electron-withdrawing reaction according to the first aspect of the present invention. When such starting compound, for example, where $R^1$ is a substituted phenyl radical, is heat-treated at 140° C. or above in the absence or presence of a high boiling point solvent capable of dissolving the said compound, there is formed the novel substance 2-hydroxy-3-(substituted phenyl)-3-butenoic acid ester (II). The reaction temperature is preferably from about 140° to 200° C., and is most preferably from 160° to 170° C., whereby the end compound can be obtained in a high yield. The solvent is not particularly limited in kind so far as it is a substance having a boiling point of 140° C. or more, but is preferably dimethyl sulfoxide, dimethyl formamide or xylene. It is preferable to carry out the reaction in the absence of solvent. According to the present process, the isolation and purification of the said end compound (II) after the reaction is quite easy.

Further, all such starting compounds of the formula (I) and (II) as mentioned previously can be subjected to the novel reaction in the presence of an electrophilic reagent according to the other aspects of the present invention. That is, when heated in the presence of an electrophilic reagent with or without the use of a solvent, the said starting compounds give the compounds of the formula (III). Examples of the electrophilic reagent used are boron trifluoride, aluminum chloride, p-toluenesulfonic acid, sulfuric acid and hydrogen chloride gas. The amount of the electrophilic reagent varies depending on the kind thereof and is not particularly limited, but is, for example, about 1/15 mole, per mole of the starting compound, in the case of sulfuric acid, about 1/10 mole in the case of p-toluenesulfonic acid, and about 1 mole in the case of boron trifluoride or $AlCl_3$. The reaction proceeds smoothly even in the absence of solvent, but may, if necessary, be carried out in the presence of such solvent as xylene, toluene, dimethyl sulfoxide or dimethyl formamide. The reaction temperature is more than 70° or 80° C., and is particularly from 100° to 250° C., preferably from 100° to 120° C. The reaction time is from 30 minutes to 8 hours, preferably from 30 minutes to 3 hours.

The compounds obtained by the present process are novel compounds (III) unknown to the literature, and, for example, where $R^1$ is a substituted phenyl radical, can be converted to 2-(substituted phenyl)-propionic acid type compounds by hydrolyzing them to free forms, followed by oxidation. Some of these compounds are useful as antiphlogistics known as ibuprofen and homologues thereof. Thus, the present invention provides an industrially advantageous process for producing such useful antiphlogistics. Several IR and NMR date of the products obtained according to the present process are as shown in the following table:

$$R^1-\overset{\overset{CH_2}{\|}}{C}-\underset{\underset{OH}{|}}{C}-COOR^2$$

| $R_1$ | $R_2$ | IR (cm$^{-1}$) | NMR (δ ppm) |
|---|---|---|---|
| cyclohexyl-phenyl- | $CH_3$ | 3470, 1730, 1214, 1110, 1078 | 3.70 (3H, s, $-CO_2CH_3$) 5.03 (1H, s, $-\overset{H}{\underset{O}{C}}-$) 5.35, 5.46 (2H, s, s, $\overset{H}{\underset{H}{\diagup}}C=C\overset{\diagup}{\diagdown}$) |
| phenoxy-tolyl- | $CH_3$ | 3480, 1733, 1584, 1570, 1486, 1222 | 3.68 (3H, s, $-CO_2CH_3$), 5.00 (1H, s, $-\overset{CO}{\underset{H}{C}}-O)^-$ 5.43, 5.48 (2H, s, s, $\overset{H}{\underset{H}{\diagup}}C=C\overset{\diagup}{\diagdown}$) |
| biphenyl- | $CH_3$ | 3460, 1731, 1596, 1242, 1208, 1112, 1078, 843 | 3.72 (3H, s, $-CO_2Me$), 5.10 (1H, s, $-\overset{CO}{\underset{H}{C}}-O^-$ 5.44, 5.56 (2H, s, s, $\overset{H}{\underset{H}{\diagup}}C=C\overset{\diagup}{\diagdown}$) |
| 4-fluoro-biphenyl- | $CH_3$ | 3463, 1731, 1600, 1499, 1223, 1160, 831 | 3.71 (3H, s, $-CO_2Me$), 5.08 (1H, s, $-\overset{CO}{\underset{H}{C}}-O)^-$ 5.44, 5.55 (2H, s, s, $\overset{H}{\underset{H}{\diagup}}C=C\overset{\diagup}{\diagdown}$) |

-continued

| R₁ | R₂ | IR (cm⁻¹) | NMR (δ ppm) |
|---|---|---|---|
| (CH₃)₂CHCH₂-C₆H₄- (isobutylphenyl) | CH₃ | 3480, 1740, 1265, 1237, 1133, 1101, 937, 872 | 0.88 (6H, d, (Me)₂C—), 2.44 (2H, d, —CH₂—)<br><br>3.61 (3H, s, —CO₂Me), 4.94 (1H, s, —C(CO)(H)—O⁻)<br><br>5.33, 5.38 (2H, s, s, CH₂=C) |
| (CH₃)₃C-C₆H₄- (tert-butylphenyl) | CH₃ | 3510, 1732, 1268, 1243, 1213, 1100, 1017, 997, 918, 840 | 1.41 (9H, s, Bᵘₜ), 3.81 (3H, s, —CO₂Me)<br><br>5.19 (1H, s, —C(CO)(H)—O⁻)<br><br>5.48, 5.59 (2H, s, s, CH₂=C) |
| 6-methoxy-2-naphthyl (CH₃O-naphthyl) | CH₃ | 3438, 1734, 1625, 1604, 1215, 1172, 1099, 1035, 1001, 910, 865 | 3.76 (3H, s, —CO₂Me), 3.98 (3H, s, —OMe)<br><br>5.26 (1H, s, —C(CO)(H)—O⁻), 5.53, 5.67 (2H, s, s, CH₂=C) |

$$R^1-\underset{R_1}{\underset{|}{CH}}-\underset{CH_3}{\overset{|}{\ }}-CO-COOR^2$$

| R₁ | R₂ | IR (cm⁻¹) | NMR (δ ppm) |
|---|---|---|---|
| 4-biphenylyl | CH₃ | 1723, 1278, 1120, 1044 | 1.43 (3H, d, —C(CH₃)—)<br><br>3.70 (3H, s, —CO₂CH₃)<br><br>4.47 (1H, q, —C(H)—) |
| 3-phenylphenyl (diphenylmethyl-type) | CH₃ | 1731, 1580, 1489, 1254, 1042 | 1.42 (3H, d, —C(CH₃)—)<br><br>3.72 (3H, s, —CO₂CH₃)<br><br>4.44 (1H, q, —C(H)—CO) |
| 4-biphenylyl | CH₃ | 1728, 1275, 1115, 1043, 765, 732 | 1.48 (3H, d, —C(CH₃)—), 3.72 (3H, s, —CO₂Me)<br><br>4.54 (1H, q, —C(H)—) |
| 4'-fluoro-4-biphenylyl (F-C₆H₄-C₆H₄-) | CH₃ | 1730, 1502, 1278, 1045, 821 | 1.49 (3H, d, —C(CH₃)—)<br><br>3.74 (3H, s, —CO₂Me)<br><br>4.55 (1H, q, —C(H)—) |

-continued

| Structure | | IR | NMR |
|---|---|---|---|
| (CH₃)₂CHCH₂-C₆H₄- | CH₃ | 1750 (shoulder), 1727, 1272, 1110, 1040 | 0.91 (6H, d, (CH₃)₂C—) 1.41 (3H, d, —C(CH₃)—) 1.86 (1H, m, —C—H) 2.42 (2H, d, —CH₂—) 3.61 (3H, s, —CO₂CH₃) 4.42 (1H, q, —C(H)—CO—) |
| (CH₃)₃C-C₆H₄- | CH₃ | 1722, 1267, 1240, 1109, 1040, 991, 915, 820 | 1.29 (9H, s, B'ᵤ) 1.44 (3H, d, —C(CH₃)—) 3.71 (3H, s, —CO₂CH₃) 4.48 (1H, q, —Ph—C(H)—) |
| CH₃O-naphthyl- | CH₃ | 1725, 1606, 1118, 1045, 1033, 862, 822, 721 | 1.60 (3H, d, —C(CH₃)—) 3.72 (3H, s, —CO₂CH₃) 3.98 (3H, s, —OCH₃) 4.70 (1H, q, —C(H)—) |

The present invention is illustrated in more detail below with reference to examples.

EXAMPLE 1

To a stirred mixture of 88.0 g. of 4-isobutylacetophenone, 119.4 g. of methyl chloroacetate and 88.0 ml. of n-hexane, 54.0 g. of sodium methoxide was gradually added over 2 hours in a nitrogen current at below 5° C. Thereafter, the mixture was gradually brought back to room temperature over a period of 5 hours, then heated to about 70° C. and further stirred for 1 hour. After cooling, the reaction liquid was charged with n-hexane, washed with water and then dried. Subsequently, the n-hexane was evaporated, and the residue was subjected to distillation to obtain 105.4 g. of methyl 3-methyl-3-(4-isobutylphenyl)-glycidate, b.p. 108°–112° C./0.2 mmHg, theoretical yield 85.0%.

32.0 Grams of the methyl 3-methyl-3-(4-isobutylphenyl)-glycidate was reacted with stirring at 150° to 170° C. for 1.5 hours in the absence of solvent. After completion of the reaction, the reaction liquid was subjected to vacuum distillation to obtain 30.4 g. of methyl 2-hydroxy-3-(4-isobutylphenyl)-3-butenoate, b.p. 113°–115° C./0.2 mmHg, theoretical yield 95.0%.

Elementary analysis (for $C_{15}H_{20}O_3$): Calculated (%): C 72.55, H 8.12. Found (%): C 72.32, H 8.15.

EXAMPLE 2

A solution of 32.0 g. of methyl 3-methyl-3-(4-isobutylphenyl)-glycidate in 50 ml. of dry dimethyl sulfoxide was reacted at 150° to 170° C. for 2.0 hours. After cooling to room temperature, the reaction liquid was poured into water and then extracted with ether. The ether layer was washed successively with water and a saturated aqueous sodium chloride solution in this order, and then dried over anhydrous magnesium sulfate. Subsequently, the ether was evaporated under reduced pressure, and the residue was subjected to distillation to obtain 29.8 g. of methyl 2-hydroxy-3-(4-isobutylphenyl)-3-butenoate, b.p. 113°–115° C./0.2 mmHg, theoretical yield 93.0%.

Elementary analysis (for $C_{15}H_{20}O_3$): Calculated (%): C 72.55, H 8.12.
Found (%): C 72.48, H 8.19.

EXAMPLE 3

A solution of 32.0 g. of methyl 3-methyl-3-(4-isobutylphenyl)-glycidate in 50 ml. of dry dimethyl formamide was reacted at 145° to 160° C. for 5 hours. After cooling to room temperature, the reaction liquid was poured into water and then extracted with ether. The ether layer was washed successively with water and a saturated sodium chloride solution in this order, and then dried over anhydrous magnesium sulfate. Subsequently, the ether was evaporated under reduced pressure, and the residue was subjected to distillation to obtain 28.8 g. of methyl 2-hydroxy-3-(4-isobutylphenyl)-3-butenoate, b.p. 113°–115° C./0.2 mmHg, theoretical yield 90.0%.

EXAMPLE 4

To a stirred mixture of 52.4 g. of 4-tert-butylacetophenone, 32.4 g. of ethyl chloroacetate and 55 ml. of n-hexane, 20.4 g. of sodium ethoxide was gradually added over a period of 1.5 hours in a nitrogen current at below 5° C. Thereafter, the mixture was gradually brought back to room temperature over a period of 5 hours, then heated to about 70° C. and further stirred for 1 hour. After cooling, the reaction liquid was charged with n-hexane, washed with water and then dried. Subsequently, the n-hexane was evaporated, and the residue was subjected to distillation to obtain 50.0 g. of ethyl 3-methyl-3-(4-tert-butylphenyl)-glycidate, b.p. 108°–111° C./0.2 mmHg, theoretical yield 67%.

37.5 Grams of the ethyl 3-methyl-3-(4-tert-butylphenyl)-glycidate was reacted with stirring at 150° to 170° C. for 1.5 hours in the absence of solvent. After completion of the reaction, the reaction liquid was subjected to vacuum distillation to obtain 15.9 g. of ethyl 2-hydroxy-3-(4-tert-butylphenyl)-3-butenoate, b.p. 115°–119° C./0.2 mmHg, theoretical yield 85.0%.

Elementary analysis (for $C_{16}H_{22}O_3$): Calculated (%): C 73.25, H 8.45. Found (%): C 73.12, H 8.53.

EXAMPLE 5

A solution of 24.8 g. of ethyl 3-methyl-3-(4-tert-butylphenyl)glycidate in 50 ml. of dry xylene was reacted at 135° to 155° C. for 8 hours. After cooling to room temperature, the reaction liquid was poured into water and then extracted with ether. The ether layer was washed successively with water and a saturated sodium chloride solution in this order, and then dried over anhydrous magnesium sulfate. Subsequently, the ether was evaporated under reduced pressure, and the residue was subjected to distillation to obtain 9.7 g. of ethyl 2-hydroxy-3-(4-tert-butylphenyl)-3-butenoate, b.p. 115°–119° C./0.2 mmHg, theoretical yield 78.2%.

Elementary analysis (for $C_{16}H_{22}O_3$): Calculated (%): C 73.25, H 8.45. Found (%): C 73.11, H 8.60.

EXAMPLE 6

40 Grams of 4-cyclohexylacetophenone and 43.2 g. of methyl chloroacetate were dissolved in a mixed solvent comprising 50 ml. of n-hexane and 50 ml. of benzene. To this solution, 27.8 g. of sodium methoxide was gradually added over a period of 1 hour with vigorous stirring in a nitrogen current at below 5° C. The resulting mixture was stirred at 5° C. for 2 hours and at room temperature for 1 hour, and then heated and refluxed with stirring for 30 minutes. After cooling, the reaction liquid was charged with hexane, and the organic layer was washed with water and dried. Subsequently, the organic solvent was evaporated under reduced pressure to obtain 50 g. of methyl 3-methyl-3-(4-cyclohexylphenyl)-glycidate, yield 91%. IR (cm$^{-1}$): 1755, 1735 (shoulder portion), 1210, 836.

50 Grams of the methyl 3-methyl-3-(4-cyclohexylphenyl)-glycidate was stirred at 150° to 170° C. for 1.5 hours in the absence of solvent to obtain 50 g. of methyl 2-hydroxy-3-(4-cyclohexylphenyl)-3-butenoate.

Elementary analysis (for $C_{17}H_{22}O_3$): Calculated (%): C 74.42, H 8.08. Found (%): C 74.25, H 7.96.

EXAMPLE 7

14.0 Grams of 4-acetylbiphenyl and 15.4 g. of methyl chloroacetate was dissolved in a mixed solvent comprising 60 ml. of benzene and 30 ml. of ether. To this solution, 10.7 g. of sodium methoxide was gradually added over a period of 30 minutes with vigorous stirring in a nitrogen current at below 8° C. The resulting mixture was stirred at 10° C. for 1 hour, at 25° C. for 1 hour and at reflux temperature for 1 hour. After cooling, the reaction liquid was charged with ether, and the organic layer was washed with water and dried. Subsequently, the organic solvent was evaporated under reduced pressure to obtain 15.0 g. of powdery methyl 3-methyl-3-(4-biphenylyl)-glycidate, m.p. 74.7°–77.0° C., yield 71%. IR (cm$^{-1}$): 1748, 1208, 1081, 770.

15.0 Grams of the methyl 3-methyl-3-(4-biphenylyl)-glycidate was dissolved in 40 ml. of dry dimethyl sulfoxide, and the resulting solution was heated at 150° to 170° C. for 2 hours. After cooling to room temperature, the reaction liquid was poured into water, and then extracted with ethyl acetate. The ethyl acetate layer was washed with water and dried over anhydrous magnesium sulfate. Subsequently, the ethyl acetate was evaporated under reduced pressure to obtain 14.0 g. of semi-crystalline methyl 2-hydroxy-3-(4-biphenylyl)-3-butenoate, yield 93%.

Elementary analysis (for $C_{17}H_{16}O_3$): Calculated (%): C 76.10, H 6.01. Found (%): C 75.95, H 6.21.

EXAMPLE 8

19.4 Grams of 3-phenoxyacetophenone and 21.6 g. of methyl chloroacetate were dissolved in 40 ml. of benzene. To this solution, 13.9 g. of sodium methoxide was gradually added over a period of 1 hour with vigorous stirring in a nitrogen current at 5° to 6° C. The resulting mixture was stirred at said temperature for 1 hour and at room temperature for 1 hour, and then refluxed with stirring for 1 hour. After cooling, the reaction liquid was charged with benzene and water, and then extracted with benzene. The benzene layer was washed with water and dried over anhydrous sodium sulfate, and then the benzene was evaporated under reduced pressure to obtain 21.0 g. of methyl 3-methyl-3-(3-phenoxyphenyl)-glycidate, yield 81%. IR(cm$^{-1}$): 1754, 1730, 1580, 1228.

21.0 Grams of the methyl 3-methyl-3-(3-phenoxyphenyl)-glycidate was dissolved in 50 ml. of dry dimethyl formamide, and the resulting solution was heated at 145° to 160° C. for 5 hours. After cooling, the reaction liquid was poured into water and then extracted with ethyl acetate. The ethyl acetate layer was washed successively with water and a saturated sodium chloride solution in this order, and then dried over anhydrous magnesium sulfate. Subsequently, the ethyl acetate was evaporated under reduced pressure to obtain 18.9 g. of methyl 2-hydroxy-3-(3-phenoxyphenyl)-3-butenoate, yield 90%.

Elementary analysis (for $C_{17}H_{16}O_4$): Calculated (%): C 71.82, H 5.67. Found (%): C 71.59, H 5.49.

EXAMPLE 9

9.5 Grams of 4-acetyl-4'-fluorobiphenyl and 9.6 g. of methyl chloroacetate were dissolved in a mixed solvent comprising 20 ml. of benzene and 10 ml. of dimethyl formamide. To this solution, 5.3 g. of sodium methoxide was gradually added over a period of 30 minutes with vigorous stirring in a nitrogen current at below 8° C. The resulting mixture was stirred at 10° C. for 1 hour, at 25° C. for 1 and at 60° C. for 1 hour. After cooling, the reaction liquid was charged with benzene and water and extracted with benzene. The benzene layer was washed with water and dried over anhydrous magnesium sulfate, and then the benzene was evaporated under reduced pressure to obtain 10.1 g. of powdery methyl 3-methyl-3-(4'-fluoro-4-biphenylyl)-glycidate, m.p. 68.6°–70.2° C., yield 79%. IR (cm$^{-1}$): 1740, 1597, 1498, 1208, 823.

10.1 Grams of the methyl 3-methyl-3-(4'-fluoro-4-biphenylyl)-glycidate was dissolved in 30 ml. of xylene, and the resulting solution was refluxed for 6 hours. After completion of the reaction, the xylene was evaporated under reduced pressure to obtain 10.0 g. of semi-crystalline methyl 2-hydroxy-3-(4'-fluoro-4-biphenylyl)-3-butenoate.

Elementary analysis (for $C_{17}H_{15}FO_3$): Calculated (%): C 71.32, H 5.28. Found (%): C 71.16, H 5.11.

EXAMPLE 10

20 Grams of 4-cyclohexylacetophenone and 26.5 g. of isopropyl chloroacetate were dissolved in 50 ml. of benzene. To this solution, 21 g. of sodium isopropoxide was added over a period of 1 hour with vigorous stirring in a nitrogen current at below 5° C. The resulting mixture was treated in the same manner as in Example 6 to obtain 23 g. of isopropyl 3-methyl-3-(4-cyclohexylphenyl)-glycidate, yield 76%.

23 Grams of the isopropyl 3-methyl-3-(4-cyclohexylphenyl)-glycidate was stirred at 150° to 170° C. for 1.5 hours in the absence of solvent to obtain 23 g. of isopropyl 2-hydroxy-3-(4-cyclohexylphenyl)-3-butenoate, Elementary analysis (for $C_{19}H_{26}O_3$): Calculated (%): C 75.46, H 8.67. Found (%): C 75.31, H 8.51.

EXAMPLE 11

14.0 Grams of 4-acetylbiphenyl and 16.4 g. of ethyl chloroacetate were dissolved in a mixed solvent comprising 60 ml. of benzene and 30 ml. of ether. To this solution, 10.7 g of sodium ethoxide was gradually added over a period of 30 minutes with vigorous stirring in a nitrogen current at below 8° C. The resulting mixture was treated in the same manner as in Example 7 to obtain 16.0 g. of ethyl 3-methyl-3-(4-biphenylyl)-glycidate.

16.0 Grams of the ethyl 3-methyl-3-(4-biphenylyl)-glycidate was stirred at 160° to 170° C. in the absence of solvent to obtain 15.9 g. of ethyl 2-hydroxy-3-(4-biphenylyl)-3-butenoate.

Elementary analysis (for $C_{18}H_{18}O_3$): Calculated (%): C 76.57, H 6.43. Found (%): C 76.49, H 6.30.

EXAMPLE 12

11.0 Grams of methyl 3-methyl-3-(3-benzoylphenyl)-glycidate was dissolved in 30 ml. of dimethyl sulfoxide, and the resulting solution was stirred at 150° C. for 2 hours. After cooling, the reaction liquid was poured into water and extracted with ethyl acetate. The ethyl acetate layer was washed with water and then dried over anhydrous magnesium sulfate. Subsequently, the ethyl acetate was evaporated under reduced pressure, and the residue was purified according to silica gel column chromatography to obtain 5.2 g. of methyl 2-hydroxy-3-(3-benzoylphenyl)-3-butenoate, yield 47%.

Elementary analysis (for $C_{18}H_{16}O_4$(296)): Calculated (%): C 72.96, H 5.44. Found (%): C 73.09, H 5.29.

EXAMPLE 13

19.0 Grams of 4-acetyl-2-fluorobiphenyl and 19.2 g. of methyl chloroacetate were dissolved in a mixed solvent comprising 40 ml. of benzene and 20 ml. of dimethyl formamide. To this solution, 10.6 g. of sodium methoxide was gradually added over a period of 1 hour with vigorous stirring in a nitrogen current at below 8° C. The resulting mixture was stirred at 10° C. for 1 hour, at 25° C. for 1 hour and at 60° C. for 1 hour. After cooling, the reaction liquid was charged with benzene and water and extracted with benzene. The benzene layer was washed with water and dried over anhydrous magnesium sulfate, and then the benzene was evaporated under reduced pressure to obtain 20.2 g. of methyl 3-methyl-3-(2-fluoro-4-biphenylyl)-glycidate, yield 79%.

20.2 Grams of the methyl 3-methyl-3-(2-fluoro-4-biphenylyl)-glycidate was dissolved in 20 ml. of dimethyl formamide, and the resulting solution was refluxed for 2 hours. After cooling, the reaction liquid was poured into water and extracted with benzene. The benzene layer was washed successively with water, an aqueous sodium bicarbonate solution and water in this order, and dried over anhydrous magnesium sulfate. Subsequently, the benzene was evaporated under reduced pressure to obtain 8.4 g. of oily methyl 2-hydroxy-3-(2-fluoro-4-biphenylyl)-3-butenoate, yield 92%.

Elementary analysis (for $C_{17}H_{15}FO_3$ (286)): Calculated (%): C 71.32, H 5.28. Found (%): C 71.11, H 5.40.

EXAMPLE 14

A mixture of 32.0 g of methyl 3-methyl-3-(4-isobutylphenyl)-glycidate and 0.1 g. of concentrated sulfuric acid was heated at 145° C. for 5 minutes. After cooling, the mixture was charged with ether and water and extracted with ether. The ether layer was washed successively with water, an aqueous sodium bicarbonate solution and water in this order, and then dried over anhydrous magnesium sulfate. Subsequently, the ether was evaporated under reduced pressure, and the residue was subjected to distillation to obtain 8.9 g. of methyl 2-hydroxy-3-(4-isobutylphenyl)-3-butenoate, b.p. 113°–115° C./0.2 mmHg, yield 28%.

Elementary analysis (for $C_{15}H_{20}O_3$): Calculated (%): C 72.55, H 8.12. Found (%): C 72.32, H 8.15.

EXAMPLE 15

29.5 Grams of ethyl 3-methyl-3-(4-tert-butylphenyl)-glycidate was dissolved in 100 ml. of o-xylene. Into this solution, dry hydrogen chloride gas was introduced at 142° C. for 10 minutes. After cooling, the reaction liquid was charged with xylene and water and extracted with xylene. The xylene layer was washed successively with water, an aqueous sodium bicarbonate solution and water in this order, and then dried over anhydrous magnesium sulfate. Subsequently, the xylene was evaporated under reduced pressure, and the residue was subjected to distillation to obtain 7.2 g. of ethyl 2-hydroxy-3-(4-tert-butylphenyl)-3-butenoate, b.p. 115°–119° C./0.2 mmHg, yield 24%.

Elementary analysis (for $C_{16}H_{22}O_3$): Calculated (%): C 73.25, H 8.45. Found (%): C 73.09, H 8.66.

EXAMPLE 16

31.0 Grams of methyl 3-methyl-3-(3-benzoylphenyl)-glycidate was dissolved in 30 ml. of dimethyl sulfoxide. To this solution was added 2.0 g. of p-toluenesulfonic acid, and the resulting mixture was heated at 145° C. for 20 minutes. After cooling, the reaction liquid was poured into water and extracted with ethyl acetate. The ethyl acetate layer was washed successively with water, an aqueous sodium bicarbonate solution and water in this order, and then dried over anhydrous magnesium sulfate. Subsequently, the ethyl acetate was evaporated under reduced pressure, and the residue was purified according to silica gel column chromatography to obtain 10.2 g. of methyl 2-hydroxy-3-(3-benzoylphenyl)-;b 3-butenoate, yield 33%.

Elementary analysis (for $C_{18}H_{16}O_4$): Calculated (%): C 72.96, H 5.44. Found (%): C 73.09, H 5.29.

EXAMPLE 17

To 24.2 g. of isopropyl 3-methyl-3-( 4-cyclohexylphenyl)-glycidate was added 0.1 g. of concentrated sulfuric acid, and the resulting mixture was heated at 150° C. for 3 minutes. After cooling, the reaction liquid was charged with ether and water and extracted with ether. The ether layer was washed successively with water, an aqueous sodium bicarbonate solution and water in this order, and then dried over anhydrous magnesium sulfate. Subsequently, the ether was evaporated under reduced pressure, and the residue was purified according to silica gel column chromatography to obtain 6.1 g. of isopropyl 2-hydroxy-3-(4-cyclohexylphenyl)-3-butenoate, yield 24%.

Elementary analysis (for $C_{19}H_{26}O_3$): Calculated (%): C 75.46, H 8.67. Found (%): C 75.19, H 8.59.

EXAMPLE 18

25.1 Grams of ethyl 3-methyl-3-(4-biphenylyl)-glycidate was dissolved in 30 ml. of dimethyl sulfoxide. To this solution was added 1.0 g. of p-toluenesulfonic acid, and the resulting mixture was heated at 145° C. for 4 minutes. After cooling, the reaction liquid was poured into water and extracted with ethyl acetate. The ethyl acetate layer was washed successively with water, an aqueous sodium bicarbonate solution and water in this order, and then dried over anhydrous magnesium sulfate. Subsequently, the ethyl acetate was evaporated under reduced pressure, and the residue was purified according to silica gel column chromatography to obtain 5.9 g. of ethyl 2-hydroxy-3-(4-biphenylyl)-3-butenoate, yield 23%.

Elementary analysis (for $C_{18}H_{18}O_3$): Calculated (%): C 76.57, H 6.43. Found (%): C 76.41, H 6.25.

EXAMPLE 19

To a solution of 8.3 g. of 6-methoxy-2-acetylnaphthalene in 50 ml. of anhydrous benzene was added 8.3 g. of methyl chloroacetate. To the resulting mixture, 4.1 g. of sodium methoxide was gradually added over a period of 1.5 hours with stirring in a nitrogen current at below 5° C. Thereafter, the mixture was stirred at 5° C. for 1 hour, at room temperature for 1 hour and at 75° C. for 1 hour. After cooling, the reaction liquid was charged with water and ethyl acetate, and then sufficiently stirred. Thereafter, the organic layer was recovered, washed with water and then dried over anhydrous magnesium sulfate. Subsequently, the organic solvent was evaporated under reduced pressure, and the resulting crude crystals were recrystallized from ethanol to obtain 7.2 g. of methyl 3-methyl-3-(6-methoxy-2-naphthyl)-glycidate, m.p. 123.8°–125.9° C., yield 68%.

Elementary analysis (for $C_{16}H_{16}O_4$): Calculated (%): C 70.57, H 5.92. Found (%): C 70.29, H 5.80.

7.2 Grams of the methyl 3-methyl-3-(6-methoxy-2-naphthyl)-glycidate was dissolved in 10 ml. of dimethyl sulfoxide, and the resulting solution was heated at 150° C. for 4 hours. After cooling, the reaction liquid was poured into water and extracted with ethyl acetate. The ethyl acetate layer was washed with water and then dried over anhydrous magnesium sulfate. Subsequently, the ethyl acetate was evaporated under reduced pressure, and the resulting crude crystals were recrystallized from ethanol to obtain 6.1 g. of methyl 2-hydroxy-3-(6-methoxy-2-naphthyl)-3-butenoate, m.p. 90.6°–92.5° C., yield 85%.

Elementary analysis (for $C_{16}H_{16}O_4$): Calculated (%): C 70.57, H 5.92. Found (%): C 70.69, H 6.09.

EXAMPLE 20

To a solution of 14.2 g. of ethyl 3-methyl-3-(3-benzoylphenyl)-glycidate in 30 ml. of toluene was added 0.2 ml. of concentrated sulfuric acid, and the resulting mixture was refluxed with stirring for 3 hours. After cooling, the reaction liquid was charged with toluene and transferred to a separating funnel, and the toluene layer was washed successively with water, an aqueous sodium bicarbonate solution and water in this order and then dried over anhydrous magnesium sulfate. Subsequently, the toluene was evaporated under reduced pressure, and the residue was purified according to silica gel column chromatography to obtain 9.1 g. of ethyl 3-methyl-3-(3-benzoylphenyl)-pyruvate, yield 64%.

Elementary analysis (for $C_{19}H_{18}O_4$ (310)): Calculated (%): C 75.53, H 5.85. Found (%): C 75.81, H 5.99.

EXAMPLE 21

To 40 g. of methyl 3-methyl-3-(4-isobutylphenyl)-glycidate was added 0.7 ml. of concentrated sulfuric acid, and the resulting mixture was stirred at 100° C. for 2.0 hours. After cooling, the reaction liquid was charged with ether and water and extracted with ether, and the ether layer was washed successively with water, an aqueous sodium bicarbonate solution and water in this order and dried over anhydrous magnesium sulfate. Subsequently, the ether was evaporated under reduced pressure, and the residue was subjected to distillation to obtain 36.4 g. of methyl 3-methyl-3-(4-isobutylphenyl)-pyruvate, b.p. 105°–108° C./0.2 mmHg, yield 91%.

Elementary analysis (for $C_{15}H_{20}O_3$): Calculated (%): C 72.55, H 8.12. Found (%): C 72.38, H 8.31.

EXAMPLE 22

To a solution of 25 g. of ethyl 3-methyl-3-(4-tert-butylphenyl)-glycidate in 100 ml. of xylene was added 18 g. of p-toluenesulfonic acid, and the resulting mixture was refluxed with stirring for 1.0 hour. After cooling, the reaction liquid was charged with 150 ml. of xylene, and the xylene layer was washed successively with water, an aqueous sodium bicarbonate solution and water in this order and then dried over anhydrous magnesium sulfate. Subsequently, the xylene was evaporated under reduced pressure, and the residue was subjected to distillation to obtain 22 g. of ethyl 3-methyl-3-(4-tert-butylphenyl)-pyruvate, b.p. 113°–115° C./0.2 mmHg, yield 88%.

Elementary analysis (for $C_{16}H_{22}O_3$ (262)): Calculated (%): C 73.25, H 8.45. Found (%): C 73.01, H 8.34.

EXAMPLE 23

To 15 g. of isopropyl 3-methyl-3-(4-cyclohexylphenyl)-glycidate was added 7.3 g. of anhydrous aluminum chloride, and the resulting mixture was stirred at 100° C. for 8 hours. After cooling, the reaction liquid was charged with ether, ice and dilute hydrochloric acid, and the extracted with ether. The ether layer was washed successively with water, an aqueous sodium bicarbonate solution and water in this order, and dried over anhydrous magnesium sulfate. Subsequently, the ether was evaporated under reduced pressure, and the resulting crude oily substance was purified according to silica gel column chromatography to obtain 7.4 g. of isopropyl 3-methyl-3-(4-cyclohexylphenyl)-pyruvate, yield 49%.

Elementary analysis (for $C_{19}H_{26}O_3$ (302)): Calculated (%): C 75.46, H 8.67. Found (%): C 75.19, H 8.43.

EXAMPLE 24

To a solution of 17 g. of methyl 3-methyl-3-(4-biphenylyl)-glycidate in 100 ml. of toluene was added 0.3 ml. of concentrated sulfuric acid, and the resulting mixture was refluxed with stirring for 3.0 hours. After cooling, the reaction liquid was charged with toluene and water, and extracted with toluene. The toluene layer was washed successively with water, an aqueous sodium bicarbonate solution and water in this order, and then dried over anhydrous magnesium sulfate. Subsequently, the toluene was evaporated under reduced pressure, and the resulting crude crystals were recrystallized from isopropyl alcohol to obtain 14.2 g. of methyl 3-methyl-3-(4-biphenylyl)-pyruvate, m.p. 84.5°–86.5° C., yield 83%.

Elementary analysis (for $C_{17}H_{16}O_3$ (268)): Calculated (%): C 76.10, H 6.01. Found (%): C 75.95, H 5.88.

EXAMPLE 25

To a solution of 23.0 g. of methyl 3-methyl-3-(4'-fluoro-4-biphenylyl)-glycidate in 40 ml. of dimethyl sulfoxide was added 12.0 ml. of a 47% boron trifluoride ether solution, and the resulting mixed solution was stirred at 120° to 130° C. for 1 hour. After cooling, the reaction liquid was poured into ice water, and extracted with ethyl acetate. The ethyl acetate layer was washed successively with water, an aqueous sodium bicarbonate solution and water in this order, and then dried over anhydrous magnesium sulfate. Subsequently, the ethyl acetate was evaporated under reduced pressure, and the resulting crude crystals were recrystallized from ethanol to obtain 17.1 g. of methyl 3-methyl-3-(4'-fluoro-4-biphenylyl)-pyruvate, m.p. 100.0°–101.6° C., yield 74%.

Elementary analysis (for $C_{17}H_{15}FO_3$): Calculated (%): C 71.32, H 5.28. Found (%): C 71.54, H 5.11.

EXAMPLE 26

To a solution of 16.3 g. of ethyl 3-methyl-3-(3-phenoxyphenyl)-glycidate in 100 ml. of toluene was added 0.3 ml. of concentrated sulfuric acid, and the resulting mixture was refluxed with stirring for 3 hours. After cooling, the reaction liquid was charged with toluene and water, and extracted with toluene. The toluene layer was washed successively with water, an aqueous sodium bicarbonate solution and water in this order, and dried over anhydrous magnesium sulfate. Subsequently, the toluene was evaporated under reduced pressure, and the resulting crude oily substance was purified according to silica gel column chromatography to obtain 13.1 g. of ethyl 3-methyl-3-(3-phenoxyphenyl)-pyruvate, yield 80%.

Elementary analysis (for $C_{18}H_{18}O_4$ (298)): Calculated (%): C 72.46, H 6.08. Found (%): C 72.64, H 6.30.

EXAMPLE 27

Into a solution of 5.0 g. of methyl 3-methyl-3-(4'-fluoro-4-biphenylyl)-glycidate in 50 ml. of xylene, hydrogen chloride gas was introduced for 1 hour under reflux with stirring. After cooling, the reaction liquid was charged with toluene and transferred to a separating funnel, and the toluene layer was washed successively with water, an aqueous sodium bicarbonate solution and water in this order, and then dried over anhydrous magnesium sulfate. Subsequently, the toluene was evaporated under reduced pressure, and the resulting crude crystals were recrystallized from ethanol to obtain 2.5 g. of methyl 3-methyl-3-(4'-fluoro-4-biphenyl)-pyruvate, m.p. 100.0°–101.6° C., yield 50%.

Elementary analysis (for $C_{17}H_{15}FO_3$): Calculated (%): C 71.32, H 5.28. Found (%): C 71.60, H 5.03.

EXAMPLE 28

To a solution of 20.5 g. of methyl 3-methyl-3-(6-methoxy-2-naphthyl)-glycidate in 100 ml. of toluene was added 0.3 ml. of concentrated sulfuric acid, and the resulting mixture was stirred at 110° C. for 3 hours. After cooling, the reaction liquid was charged with toluene and transferred to a separating funnel, and the toluene layer was washed successively with water, an aqueous sodium bicarbonate solution and water in this order, and then dried over anhydrous magnesium sulfate. Subsequently, the toluene was evaporated under reduced pressure, the residue was purified according to silica gel column chromatography, and the resulting crude crystals were recrystallized from ether-petroleum benzine to obtain 10.3 g. of methyl 3-methyl-3-(6-methoxy-2-naphthyl)-pyruvate, m.p. 53.2°–54.9° C., yield 50%.

Elementary analysis (for $C_{16}H_{16}O_4$): Calculated (%): C 70.57, H 5.92. Found (%): C 70.39, H 5.81.

EXAMPLE 29

To a solution of 23.0 g. of methyl 3-methyl-3-(2-fluoro-4-biphenylyl)-glycidate in 40 ml. of xylene was added 0.3 ml. of concentrated sulfuric acid, and the resulting mixture was stirred at 125° C. for 2 hours. After cooling, the reaction liquid was charged with 100 ml. of xylene and transferred to a separating funnel, and the xylene layer was washed successively with water, an aqueous sodium bicarbonate solution and water in this order, and then dried over anhydrous magnesium sulfate. Subsequently, the xylene was evaporated under reduced pressure, and the residue was purified according to silica gel column chromatography to obtain 17.2 g. of methyl 3-methyl-3-(2-fluoro-4-biphenylyl)-pyruvated, yield 75%.

Elementary analysis (for $C_{17}H_{15}FO_3$ (286)): Calculated (%): C 71.32, H 5.28. Found (%): C 71.06, H 5.43.

EXAMPLE 30

To 40 g. of methyl 3-methyl-3-(4-isobutylphenyl)-3-butenoate was added 0.7 ml. of concentrated sulfuric acid, and the resulting solution was stirred at 100° C. for 2.0 hours. After cooling, the reaction liquid was charged with ether and water and extracted with ether, and the ether layer was washed successively with water, an aqueous sodium bicarbonate solution and water in this order, and then dried over anhydrous magnesium sulfate. Subsequently, the ether was evaporated under reduced pressure, and the residue was subjected to distillation to obtain 36.4 g. of methyl 3-methyl-3-(4-isobutylphenyl)-pyruvate, b.p. 105°–108° C./0.2 mmHg, yield 91%.

Elementary analysis (for $C_{15}H_{20}O_3$): Calculated (%): C 72.55, H 8.12. Found (%): C 72.41, H 8.34.

EXAMPLE 31

To a solution of 25 g. of ethyl 3-methyl-3-(4-tert-butylphenyl)-3-butenoate in 100 ml. of xylene was added 18 g. of p-toluenesulfonic acid, and the resulting mixture was refluxed with stirring for 1.0 hour. After cooling, the reaction liquid was charged with 150 ml. of xylene, and the xylene layer was washed successively with water, an aqueous sodium bicarbonate solution and water in this order, and then dried over anhydrous magnesium sulfate. Subsequently, the xylene was evaporated under reduced pressure, and the residue was subjected to distillation to obtain 22 g. of ethyl 3-methyl-3-(4-tert-butylphenyl)-pyruvate, b.p. 113°–115° C./0.2 mmHg, yield 88%.

Elementary analysis (for $C_{16}H_{22}O_3$): Calculated (%): C 73.35, H 8.45. Found (%): C 73.01, H 8.34.

EXAMPLE 32

To 15 g. of isopropyl 3-methyl-3-(4-cyclohexylphenyl)-3-butenoate was added 7.3 g. of anhydrous aluminum chloride, and the resulting mixture was stirred at 100° C. for 8 hours. After cooling, the reaction liquid was charged with ether, ice and dilute hydrochloric acid, and then extracted with ether. The ether layer was washed successively with water, an aqueous sodium bicarbonate solution and water in this order, and then dried over anhydrous magnesium sulfate. Subsequently, the ether was evaporated under reduced pressure, and the resulting crude oily substance was purified according to silica gel column chromatography to obtain 7.4 g. of isopropyl 3-methyl-3-(4-cyclohexylphenyl)-pyruvate, yield 49%.

Elementary analysis (for $C_{19}H_{26}O_3$ (302)): Calculated (%): C 75.46, H 8.67. Found (%): C 75.31, H 8.48.

EXAMPLE 33

To a solution of 17 g. of methyl 3-methyl-3-(4-biphenylyl)-3-butenoate in 100 ml. of toluene was added 0.3 ml. of concentrated sulfuric acid, and the resulting mixture was refluxed with stirring for 3.0 hours. After cooling, the reaction liquid was charged with toluene and water, and extracted with toluene. The toluene layer was washed successively with water, an aqueous sodium bicarbonate solution and water in this order, and then dried over anhydrous magnesium sulfate. Subsequently, the toluene was evaporated under reduced pressure, and the resulting crude crystals were recrystallized from isopropyl alcohol to obtain 14.2 g. of methyl 3-methyl-3-(4-biphenylyl)-pyruvate, m.p. 84.5°–86.5° C., yield 83%.

Elementary analysis (for $C_{17}H_{16}O_3$ (268)): Calculated (%): C 76.10, H 6.01. Found (%): C 75.91, H 6.30.

EXAMPLE 34

To a solution of 23.0 g. of methyl 3-methyl-3-(4'-fluoro-4-biphenylyl)-3-butenoate in 40 ml. of dimethyl sulfoxide was added 12.0 ml. of a 47% boron trifluoride ether solution, and the resulting mixed solution was stirred at 120° to 130° C. for 1 hour. After cooling, the reaction liquid was poured into ice water and extracted with ethyl acetate. The ethyl acetate layer was washed successively with water, an aqueous sodium bicarbonate solution and water in this order, and then dried over anhydrous magnesium sulfate. Subsequently, the ethyl acetate was evaporated under reduced pressure, and the resulting crude crystals were recrystallized from ethanol to obtain 17.1 g. of methyl 3-methyl-3-(4'-fluoro-4-biphenylyl)-pyruvate, m.p. 100.0°–101.6° C., yield 74%.

Elementary analysis (for $C_{17}H_{15}FO_3$): Calculated (%): C 71.32, H 5.28. Found (%): C 71.54, H 5.16.

EXAMPLE 35

To a solution of 16.3 g. of ethyl 3-methyl-3-(3-phenoxyphenyl)-3-butenoate in 100 ml. of toluene was added 0.3 ml. of concentrated sulfuric acid, and the resulting mixture was refluxed with stirring for 3.0 hours. After cooling, the reaction liquid was charged with toluene and water, and extracted with toluene. The toluene layer was washed successively with water, an aqueous sodium bicarbonate solution and water in this order and then dried over anhydrous magnesium sulfate. Subsequently, the toluene was evaporated under reduced pressure, and the resulting crude oily substance was purified according to silica gel column chromatography to obtain 13.1 g. of ethyl 3-methyl-3-(3-phenoxyphenyl)-pyruvate, yield 80%.

Elementary analysis (for $C_{18}H_{18}O_4$ (298)): Calculated (%): C 72.46, H 6.08. Found (%): C 72.41, H 6.32.

EXAMPLE 36

Into a solution of 5.0 g. of methyl 3-methyl-3-(4'-fluoro-4-biphenylyl)-3-butenoate in 50 ml. of xylene, hydrogen chloride gas was introduced for 1 hour under reflux with stirring. After cooling, the reaction liquid was charged with toluene and transferred to a separating funnel, and the toluene layer was washed successively with water, an aqueous sodium bicarbonate solution and water in this order, and then dried over anhydrous magnesium sulfate. Subsequently, the toluene was evaporated under reduced pressure, and the resulting crude crystals were recrystallized from ethanol to obtain 2.5 g. of methyl 3-methyl-3-(4'-fluoro-4-biphenylyl)-pyruvate, m.p. 100.0°–101.6° C., yield 50%.

Elementary analysis (for $C_{17}H_{15}FO_3$): Calculated (%): C 71.32, H 5.28. Found (%): C 71.14, H 5.05.

EXAMPLE 37

To a solution of 23.0 g. of methyl 3-methyl-3-(2-fluoro-4-biphenylyl)-3-butenoate in 40 ml. of xylene was added 0.3 ml. of concentrated sulfuric acid, and the resulting mixture was stirred at 125° C. for 2 hours. After cooling, the reaction liquid was charged with 100 ml. of xylene and transferred to a separating funnel, and the xylene layer was washed successively with water, an aqueous sodium bicarbonate solution and water in this order, and then dried over anhydrous magnesium sulfate. Subsequently, the xylene was evaporated under reduced pressure, and the residue was purified according to silica gel column chromatography to obtain 17.2 g. of methyl 3-methyl-3-(2-fluoro-4-biphenylyl)-pyruvate, yield 75%.

Elementary analysis (for $C_{17}H_{15}FO_3$ (286)): Calculated (%): C 71.32, H 5.28. Found (%): C 71.06, H 5.43.

EXAMPLE 38

To a solution of 11.8 g. of butyl 3-methyl-3-(3-benzoylphenyl)-3-butenoate in 40 ml. of toluene was added 0.15 ml. of concentrated sulfuric acid, and the resulting mixture was stirred at 100° C. for 4 hours. After cooling, the reaction liquid was charged with toluene and transferred to a separating funnel, and the toluene layer was washed successively with water, an aqueous sodium bicarbonate solution and water in this order, and then dried over anhydrous magnesium sulfate. Subsequently, the toluene was evaporated under reduced pressure, and the residue was purified according to silica gel column chromatography to obtain 6.3 g. of butyl 3-methyl-3-(3-benzoylphenyl)-pyruvate.

Elementary analysis (for $C_{21}H_{22}O_4$ (338)): Calculated (%): C 74.53, H 6.55. Found (%): C 74.38, H 6.41.

EXAMPLE 39

To a solution of 25 g. of methyl 2-hydroxy-3-(6-methoxy-2-naphthyl)-3-butenoate in 100 ml. of xylene was added 18 g. of p-toluenesulfonic acid, and the resulting mixture was stirred at 140° C. for 1 hour. After cooling, the reaction liquid was charged with 150 ml. of xylene, and the xylene layer was washed successively with water, an aqueous sodium bicarbonate solution and water in this order, and then dried over anhydrous magnesium sulfate. Subsequently, the xylene was evaporated under reduced pressure, the residue was purified according to silica gel column chromatography, and the resulting crude crystals were recrystallized from ether-petroleum benzine to obtain 18.2 g. of methyl 3-methyl-3-(6-methoxy-2-naphthyl)-pyruvate, m.p. 53.2°–54.6° C., yield 72%.

Elementary analysis (for $C_{16}H_{16}O_4$): Calculated (%): C 70.57, H 5.92. Found (%): C 70.34, H 5.80.

What we claim is:

1. A hydroxy-butenoic acid compound of the general formula:

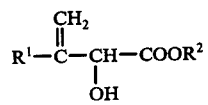

wherein $R^1$ is 4-biphenylyl, 4-cyclohexylphenyl, 3-phenoxyphenyl, 4'-fluoro-4-biphenylyl, 2-fluoro-4-biphenylyl, 3-benzoylphenyl or 6-methoxynaphthyl, and $R^2$ is a lower alkyl group.

* * * * *